United States Patent [19]

Amendolia

[11] Patent Number: 4,925,451
[45] Date of Patent: May 15, 1990

[54] I.V. FLOW CONTROL DEVICE

[76] Inventor: Pasquale J. Amendolia, P.O. Box 475, St. James, N.Y. 11780

[21] Appl. No.: 182,421

[22] Filed: Apr. 18, 1988

[51] Int. Cl.$^5$ .............................................. A61M 5/05
[52] U.S. Cl. ................................... 604/246; 604/248; 137/501
[58] Field of Search ............... 604/248, 246, 257, 118, 604/122, 32; 251/208, 125; 137/501

[56] References Cited

U.S. PATENT DOCUMENTS

| 3,323,774 | 6/1967 | Wilson | 604/251 |
|---|---|---|---|
| 3,620,500 | 11/1971 | Santomieri | 604/246 |
| 3,783,892 | 1/1974 | Joesting . | |
| 3,785,378 | 1/1974 | Stewart | 604/248 |
| 3,877,428 | 4/1975 | Seagle et al. | 604/248 |
| 3,886,968 | 6/1975 | Murrell . | |
| 4,043,332 | 8/1977 | Metcalf . | |
| 4,142,523 | 3/1979 | Stegeman | 604/246 |
| 4,316,460 | 2/1982 | Genese et al. . | |
| 4,428,397 | 1/1984 | Bron | 137/501 |
| 4,515,588 | 5/1985 | Amendolia . | |
| 4,594,058 | 6/1986 | Fischell . | |
| 4,604,090 | 8/1986 | Reinicke . | |
| 4,769,012 | 9/1988 | Quanq et al. | 604/248 |
| 4,789,000 | 12/1988 | Aslanian | 604/248 |
| 4,802,506 | 2/1989 | Aslanian | 604/246 |
| 4,807,660 | 2/1984 | Aslanian | 604/248 |

Primary Examiner—John D. Yasko
Assistant Examiner—Kathleen A. Daley
Attorney, Agent, or Firm—Leonard Belkin

[57] ABSTRACT

A flow selector and regulator for use in an I.V. administration arrangement which includes the capability of establishing the flow rate without calibration at the time of use and then automatically maintaining that flow rate regardless of changes in fluid pressure in either or both of upstream or downstream of the regulator. The regulator utilizes a diaphragm which is not subject to stretching or material stress prior to use to control an orifice. The regulator is capable of being calibrated at the time of manufacturer directly in terms of flow rate, something which is not possible in prior such devices. The diaphragm is clamped at the rim and has an arcuate torus facing the inlet and a bulbous central section which controls flow through an outlet orifice. Liquid bypasses the diaphragm through the rim. Other embodiments incorporate the regulator into a drip chamber and reduces the number of parts of the regulator to three members which can be snapped together.

18 Claims, 5 Drawing Sheets

I.V. FLOW CONTROL DEVICE

BACKGROUND OF THE INVENTION

This invention relates to apparatus for regulating the flow of a liquid being delivered to a patient such as in the administration of intravenous (I.V.) solutions, and more particularly to disposable flow regulation apparatus which will establish and maintain a rate of flow which will not be altered by changes in elevation of the point of administration, venous pressure, or the level of the supply liquid.

The administration of glucose, saline, or other solutions with or without pharmaceuticals to patients in hospitals or elsewhere is a common mode of treatment capable of fulfilling a variety of medical requirements. In a typical arrangement for such administration there is utilized a stand for supporting a reservoir containing a measured amount of the liquid, tubing extending down from the reservoir, and, for intravenous feeding, an implement which would include a needle attached to the end of the tube for delivering the liquid into the body of the patient.

The reservoir is ordinarily held well above the point of administration so that gravity is relied upon to provide the necessary pressure to insure continuous flow of the liquid. A valve in the tubing not only permits fluid flow to be initiated or terminated at will, but also regulates the rate of flow so that the nurse or other medical technician can set the rate of flow as prescribed by the attending physician. Customarily a drip chamber is provided to remove air and permit clear visualization of the rate of flow by counting the number of drops per unit of time.

In my U.S. Pat. No. 4,515,588 there is shown a regulator for such use which is capable of maintaining the selected flow rate of such solutions regardless of changes in fluid pressure caused by changes in head. In that patent, the drip chamber is relied upon to indicate the flow rate to be maintained.

The aforementioned patented device is made typically of six or more parts requiring assembly, and some of the assembly requires stretching of the membrane contained therein. Since the regulator is disposable, that is, it is disposed of after a single use, the number of parts involved and the complexity of the assembly produces a cost factor which in some situations could limit its availability.

Furthermore, when the patented regulator is put into use, the technician establishes the flow rate by turning the dial or knob on it until the desired drip rate is obtained in the drip chamber. The regulator uses a screw type metering valve which distorts a rubber diaphragm into a tapered orifice thus varying the orifice and metering the flow into the regulating chamber. The distortion is unpredictable and the control range can vary and some initial drift can even occur for a given setting of the control knob. As a result, it is not possible to establish a uniform calibration at the time of manufacture so that the dial can be set to read in terms of flow rate. In addition, since the diaphragm is put under stress by being stretched at the time of assembly, during the shelf life of the regulator its flow regulation characteristics can drift.

There are regulating devices on the market having numbers on their dial areas but these numbers are only valid for a specific head height. In fact, one such manufacturer has supplied a paper ruler with each device to facilitate setting the exact height required that will make the numbers indicated valid. Any change in this dimension voids the setting values. To make these numbers meaningful the fluid level must not change in the supply bag and the output end must not change position and the patient's venous pressure must not change.

In addition, a variety of other patented devices are concerned with the regulation of liquid flow.

In U.S. Pat. No. 3,783,892 there is shown a long timing fluidic device which employs either a spring with a diaphragm or multiple diaphragms to control fluid flow.

In U.S. Pat. No. 3,886,968 a flow control device is disclosed which utilizes a spring in combination with a diaphragm. The spring remains in contact with the diaphragm.

In U.S. Pat. No. 4,043,332 there is described a constant flow rate liquid medicament administering device which utilizes a diaphragm with a valve stem attached thereto and thereby loading the diaphragm.

In U.S. Pat. No. 4,316,460 a gravitational flow system is illustrated which employs a seated diaphragm which becomes unseated upon the application of the secondary liquid.

In U.S. Pat. No. 4,594,058 there is disclosed a single valve diaphragm pump using a diaphragm attached to a cylinder actuated by a magnetic solenoid.

In U.S. Pat. No. 4,604,090 is illustrated an implantable medication infusion device which utilizes a diaphragm having a magnet mounted thereon to adjust the diaphragm.

The above arrangements are all complex, expensive to manufacture and assemble, and in some cases there would appear to be the strong possibility that diaphragm characteristics can change substantially during shelf lives.

SUMMARY OF THE INVENTION

In my present invention there is provided a disposable flow regulator suitable for I.V. applications having fewer parts than the regulator in my previously identified patent, can be assembled more readily by mass production techniques, and has certain improved features such as less change in flow characteristics during the normally expected shelf life for such devices, as well as being easier to use by health care workers such as nurses and even less experienced persons such as persons engaged in home care.

A preferred embodiment of this invention consists of inlet and outlet members for receiving and discharging liquid, respectively, and a diaphragm mounted between and separating the inlet member from the outlet member including provision to permit flow of liquid through a portion of the diaphragm. The diaphragm comprises a membrane surrounded by a rim clamped between the inlet and outlet members, the membrane being shaped in the form of an arcuate torus the outer surface of which faces the inlet member, and the portion of the membrane surrounded by the ridge forming a bulbous section the outer surface of which faces the outlet member.

The inlet member has an inlet orifice surrounded by an annular boss extending toward the membrane while the outlet member has an outlet orifice adjacent the bulbous section which regulates the flow through the orifice. Included is a device for selecting a rate of flow of the liquid through the diaphragm, with the bulbous section moving in response to differential liquid pressure across the membrane to maintain constant the flow rate selected by the selecting device.

In the arrangement just described, the membrane in its resting position, that is, its configuration in the absence of any liquid present, is not in contact with any part of the regulator. As a result, the membrane is not under any stress and its elastic properties will not change significantly during the expected maximum shelf life of the apparatus.

The present invention meters the flow of a liquid by positioning a tapered groove for communication over a pair of openings thus always presenting a predictable dimension for a specific position because the tapered groove is molded to a specific dimension and is reproducible from unit to unit. Since there is no distortion of rubber or other elastic material used to create the metering, the settings are relatively drift free.

Because the metering system of the present invention is reproducible, it is possible to put markings on the metering dial that can indicate a particular flow rate for that setting. This combined with the very important fact that the regulating portion of the device can adjust the flow to compensate for variations in input or output head changes, allows manufacture of a device whereby the desired flow rate can simply be set and the rate will remain constant.

Furthermore, the arrangement is capable of being calibrated at the factory for flow rates corresponding to indices on the regulator independent of the height of the reservoir and the vertical distance down to the site of injection at the time the regulator is put into use. In other words, the present invention includes means independent of external calibration for setting the flow rate, by which is meant herein, that once the regulator is manufactured the calibration is fixed so that no further calibration at the time of, or prior to, use is required.

The dial can be set to a particular value without the need to select some specific height as a reference and because of the compensation system, the value will still be valid over the normal operating range, usually several feet of position changes.

In the manufacture of my patented device, a system is required to tighten the control knob to some predetermined setting after the assembly resulting in additional manufacturing steps.

In contrast, the present invention comprises only a few parts which can readily be assembled using available mass production techniques without the use of any human labor.

In another embodiment of this invention the number of parts involved is reduced to only three while retaining substantially all of the advantages of the first embodiment It is therefore a principal object of this invention to provide improved apparatus for selecting and maintaining the flow rate of a liquid.

Other objects and advantages of this invention will hereinafter become obvious from the following description of preferred embodiments of this invention.

DETAILED DESCRIPTION OF THE PREFERRED EMBODIMENTS

Figures 1, 2, 3:
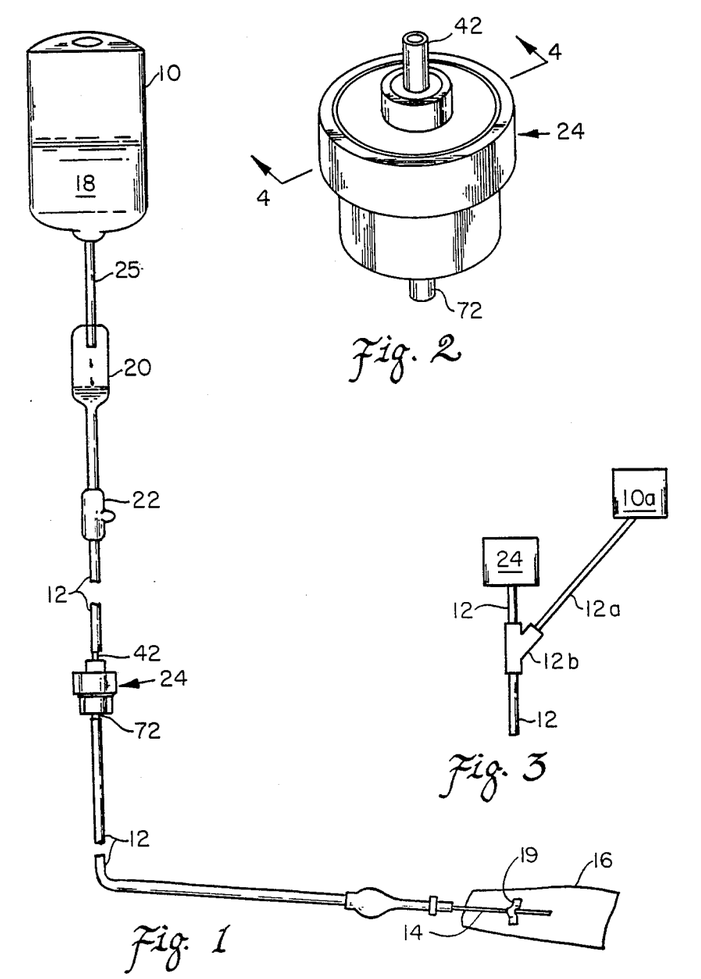
FIG. 1 is a partially schematic view of an I.V. administration system employing a preferred embodiment of this invention.
FIG. 2 is an isometric view of a preferred embodiment of a flow regulator embodying the principles of this invention.
FIG. 3 is a schematic view of a piggyback application of the regulator shown in FIGS. 1 and 2.

An I.V. administration system incorporating a preferred embodiment of this invention consists, as shown in FIG. 1, of a reservoir 10 connected through tubing 12 to a hypodermic needle 14 which is inserted into the arm 16 of a patient for the delivery of the parenteral liquid 18 stored in reservoir 10. Tape 19 may be employed to hold needle 14 in place during use.

Tubing 12 is provided with a drip chamber 20, a flow control valve 22, and the flow regulator 24 which incorporates the novel features of this invention. Reservoir 10 is connected to drip chamber 20 through a tube 25.

Reservoir 10 may be a rigid container which is vented so that air can replace liquid 18 as it drains out or may be a sealed collapsible bag where no venting is required.

Drip chamber 20, being of transparent material, as is understood in the art, performs the primary function of permitting the calculation of flow rate by the counting of drops, although it also may serve to remove any air bubbles which might be present in the liquid.

Flow control valve 22 permits the adjustable clamping of tubing 12 passing through, and conventionally it is used to establish the drip rate at the desired value. When regulator 24 is employed, however, valve 22 may be dispensed with if desired since regulator 24 has a zero flow state. Valve 22 in the form of an ON/OFF clamp may be utilized so as not to disturb a setting on regulator 24.

Referring to FIGS. 2—5, regulator 24 consists of an inlet member 26, an outlet member 28, a diaphragm 32 clamped between the inlet and outlet members just identified, and flow rate selector 34. Between flow rate selector 34 and inlet member 26 is a metering gasket 36.

Figure 4:
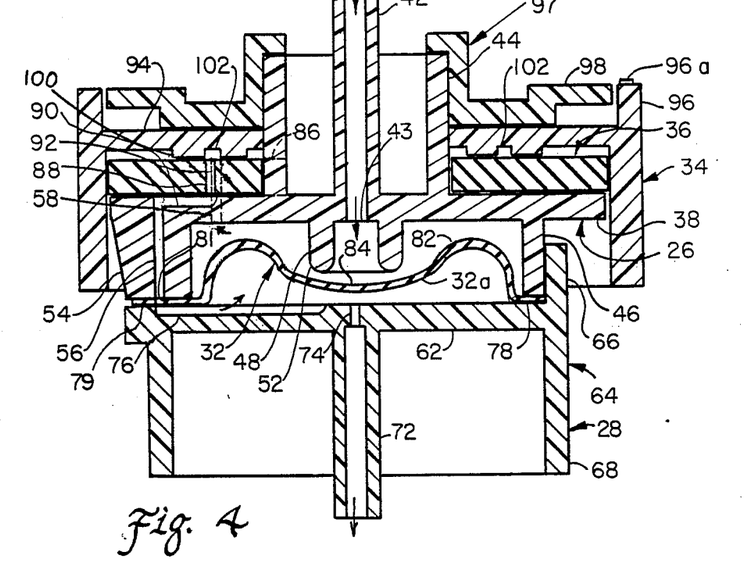
FIG. 4 is a section view taken along 4—4 of FIG. 2.

Inlet member 26 consists of a circular disk 38 from which extends up an inlet tube 42 surrounded by a cylindrical section 44. Inlet tube 42 is connected to and receives liquid in tube 12 coming from valve 22 or drip chamber 20. Extending down from disk 38 is a cylindrical section 46 which at the bottom clamps diaphragm 32 against outlet member 28 as will be later more particularly described. Also extending down from disk 38 is a cylindrical locating boss 48, with a rounded annular extremity 52 for a purpose also to be later described.

Inlet member 26 is provided with a key 54 having a passageway 56. Through disk 38 is another passageway 58 spaced from passageway 56 closer to the central axis of member 26 and angularly offset.

Outlet member 28 consists of a circular disk 62 with an outer cylindrical section 64 having an upper portion 66 in contact with the outer surface of cylindrical section 46 of inlet member 26 as illustrated, and a lower portion 68 extending downwardly.

An outlet tube 72 extends downwardly for directing liquid from outlet orifice 74 into the portion of tube 12 connected to needle 14.

The upper surface of disk 62 is provided with a radially extending channel 76 which is aligned at one end with passageway 56 in key 54 and is along a portion of the underside of diaphragm 32 as shown.

Figure 5:
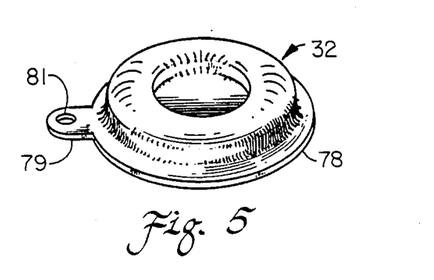
FIG. 5 is an isometric view of the diaphragm employed in the embodiment of FIGS. 1-4.

Diaphragm 32 consists of an annular flange 78 which is held in place by the assembly o inlet and outlet members 26 and 28, respectively, in the manner illustrated and already noted, surrounding a membrane 32a to be described below. Flange 78 is provided with a key 79 (engaging cylindrical section 66) having a passageway 81 aligned with passageway 56 in key 54 of member 26. Membrane 32a is circular and may be constructed of a rubber material and has the shape shown consisting of an upwardly extending arcuate torus 82 surrounding a downwardly extending bulbous section 84. In FIG. 4, diaphragm 32 is shown in its resting position, that is, in the absence of any liquid, in other words, as the regulator 24 would be shipped and stored ready to be put into use. Thus diaphragm 32 is not subject to any stress imposed by any members in contact with it outside of the flange so that its shelf life with retention of its elastic qualities at the time of manufacture will be far longer than if subject to any distorting forces imposed over a period of time, such as if it were stretched during assembly of regulator 24.

Metering gasket 36, which may also be constructed of rubber or similar material, may be provided with a key 86 to engage cylindrical section 44 of inlet member 26 to insure that it will remain in fixed relationship with respect to the latter.

Figure 4A:
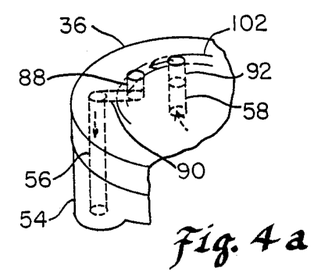
FIG. 4a is a partial, isometric view in schematic form of a portion of the regulator shown in FIG. 4.

As also seen in FIG. 4a, gasket 36 is provided with a pair of spaced passageways 88 and 92 parallel to each other located along a common circumference. Passageway 92 is aligned with passageway 58 in disk 38 of member 26 while passageway 88 terminates at one end in communication with a radially extending groove 90 in the top surface of disk 38. The other end of groove or channel 90 communicates with passageway 56 in key 54 of member 26. Later it will be described how communication between passageways 88 and 92 is provided above gasket 36. Key 79 of flange 78, key 86 of gasket 36, and key 54 of member 26 insure alignment of the passageways and channel 76 in the manner described.

Flow selector 34 is a rotatable member consisting of a circular disk 94 within and surrounded by a cylindrical section 96 the outer surface of which may be knurled or ribbed since selector 34 by manual rotation selects the rate of flow of the liquid through regulator 24. An annular stationary member 97 is attached to stationary inlet member 26 at cylindrical section 44 and has a rim 98 which comes close to cylindrical section 96 of flow selector 34. Rim 98 may be calibrated with flow rate markings and the top surface of section 96 may have an index mark 96a for showing the rate of flow selected on rim 98. If desired, the calibrations may be placed on the outer surface of selector 34 with the index on rim 98.

It may be appropriate to mention at this point that an important feature of this invention is that regulator 24 may be employed to set the flow rate desired by the adjustment of flow selector 34 and then the apparatus will maintain that flow rate within very close limits regardless of any changes in liquid pressure in either or both of the inlet and outlet to regulator 24.

Figure 6:
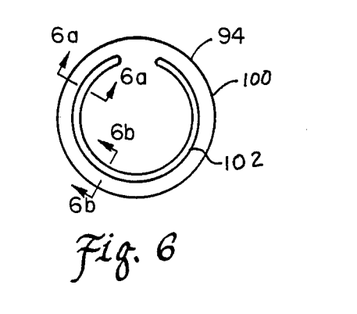
FIG. 6 is a view of the projection on the lower face of the circular disk of the flow selector containing the tapered groove.
Figure 6A:
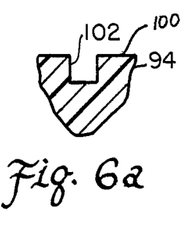
FIG. 6a and 6b are views, respectively, taken along 6a—6a and 6b—6b of FIG. 6.
Figure 6B:
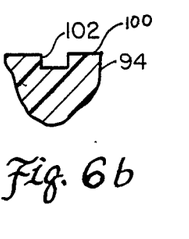

The manner by which flow selector 34 sets the flow rate will now be described. It was noted that selector 34 has a circular disk 94 which is in contact with the top surface of metering gasket 36 which is keyed against rotation with inlet member 26. The underside of disk 94 making this contact is provided with a projection 100 having a circular, tapered groove 102 (seen also in FIG. 6) of varying depth (see FIGS. 6a and 6b) arranged to provide communication between passageways 88 and 92 in metering gasket 36. As flow selector 34 is rotated, the depth of groove 102 making this communication between the two passageways changes, with resultant changes in cross sectional area thus permitting increases or decreases in liquid flow depending upon the rotational position of selector 34. In the description of the operation of regulator 24 this will be further discussed. Suffice it to say at this point that the arrangement just described is so effective that the dial settings on rim 98 or on the outer surface of cylindrical section 96 corresponding with the flow through the apparatus can be set at the factory with great assurance that it will be accurate within accepted standards in the industry regardless of the heights of the reservoir and the site of the injection relative to regulator 24 within normally anticipated ranges at the time regulator 24 is put into use.

Figure 7:
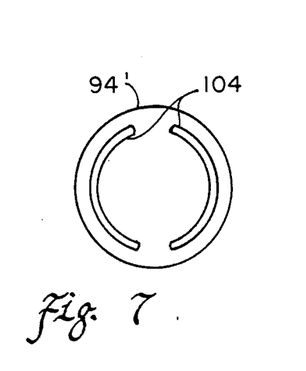
FIG. 7 and 8 are views similar to FIG. 6 showing alternative groove arrangements.
Figure 8:
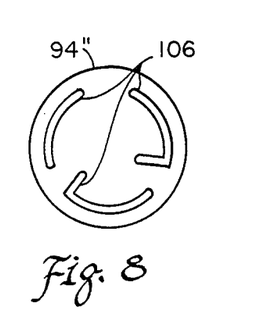

FIGS. 7 and 8 show other possible arrangements of grooves 104 and 106 on the underside of disks 94' or 94" which are possible. The selection of groove shapes would be determined by the ranges of flow rates to be made available for particular applications, and whether more than one range might want to be included on a single disk 94.

With regard to diaphragm 32, it has already been noted that it would be made of rubber or similar material and that in its resting position in the absence of liquid in the system it would not contact the lower extremity 52 of annular boss 48 or disk 62, or any other part of regulator 24, except for flange 78 which holds it in place. The portion of diaphragm 32 surrounded by flange 78, that is, membrane 32a separates the liquid entering regulator 24 and passing through inlet orifice 43 from the liquid below diaphragm 32 leaving regulator 24 by way of outlet orifice 74. From the shape of diaphragm 32 as described, the membrane portion has the characteristic that as the pressure above increases with respect to the pressure below, bulbous section 84 moves down as the result of arcuate torus 82 rolling, rather than any stretching of the material from which diaphragm 32 is constructed. In the event of a reversal of this pressure differential, the opposite action occurs. From an overall point of view it may be stated that as bulbous section 84 approaches outlet orifice 74 there is a restriction in the rate of flow out of, and thus through regulator 24, and vice versa. As a consequence of the foregoing, there is a close correlation of diaphragm movement to flow rate which makes it possible to establish the flow rate using flow selector 34.

In the operation of regulator 24, clamp 22 in line 22 is merely fully opened as regulator 24 takes over full control of establishing the rate of flow as the result of first positioning flow selector 34 to the rate indicated on rim 98 or section 96 and then maintaining that flow rate regardless of changes in liquid pressures.

Referring to FIGS. 4 and 4a in particular, the liquid enters regulator 24 through inlet pipe 42, passing through orifice 43 into the inlet chamber above diaphragm 32. As shown by arrows the liquid passes up through passageways 58 and 92 into tapered groove 102 which communicates with passageway 88 in flow control gasket 36. The rate of flow is established by the depth of the part of groove 102 interconnecting passageways 92 and 88, which, as previously noted, is selected by rotating flow selector 34 according to the calibration markings on rim 98 or section 96.

The liquid flows down passageway 88 into groove 90 to passageways 56 and 81 and hence into the outlet chamber under membrane 32a by way of groove or channel 76. The liquid leaves regulator 24 by passing out through outlet orifice 74 through tube 72 into tube 12 and then to the needle 14. With liquid flowing in the system, bulbous section 84 of diaphragm 32 rolls down toward orifice 74 where it controls flow therethrough in the manner previously described. When the pressure above diaphragm 32 increases with respect to flow below it, section 84 moves down further restricting flow out and increasing the pressure just below causing an upward adjustment in section 84, thereby effectively maintaining a constant rate of flow through regulator 24 regardless of changes in liquid pressure both above and below regulator 24 such as might be caused by raising or lowering bag 10 or raising or lowering of arm 16 of the patient.

The purpose of boss 48 extending downwardly to a point just above diaphragm 32 is to act first as a check valve, in case there should be an increase in pressure of the liquid under diaphragm 32 which could cause reversal of flow through regulator 24. It is sometimes necessary in I.V. administration systems to interrupt the administration in order to substitute another medicament for a short period of time before returning to the primary medicament. This ordinarily would be accomplished, as seen in FIG. 3, by adding a separate I.V. line 12a leading to pipe 12 through a "Y" 12b below regulator 24, placing the new bag 10a above bag 10 to insure the replacement, sometimes referred to as a piggyback. The check valve resulting from diaphragm 32 contacting boss 48 due to increase pressure below prevents the reversal of flow through regulator 24. When secondary bag 10a becomes empty, regulator 24 returns automatically to normal operation without any intervention by a nurse or technician.

In addition, boss 48 acts as an anti-bolus device. Sometimes, as the result of a sudden large change in pressure drop across regulator 24, such as might be caused by the piggyback operation described above, or sudden change in bag elevation or venous pressure within the patient, membrane 32a or bulbous section 84 may move up toward orifice 43. Without the presence of boss 48, medication would fill up the space under membrane 32a above outlet orifice 74. When membrane 32a drops down toward outlet orifice 74 when operation returns to normal there could be a surge or bolus of medication dumped through orifice 74 and delivered to the patient. This could be harmful in some cases. The presence of boss 48 extending downwardly as shown prevents a buildup of medication above outlet orifice 74 by preventing membrane 32a from moving all the way up, thus this arrangement is referred to herein as an anti-bolus device.

Careful studies of the operation of diaphragm 32, and bulbous section 84, in particular, designed to determine the exact manner in which they function to control the rate of liquid flow through orifice 74, has shown that in the ranges of pressures associated with I.V. administration, section 84 in fact opens and shuts orifice 74, and the rate or frequency at which this occurs closely corresponds to the rate of flow through that orifice. The opening and closing of orifice 74 by the fluttering action of section 84 causes a low buzzing sound, barely audible. This suggests that the rate of flutter of section 84 as detected by a transducer can be employed, if desired, to measure and display electronically, preferably in digital format, the rate of flow through regulator 24.

From the foregoing description of the preferred embodiment and its operation, certain additional advantages of this invention over that in my earlier patent and other devices presently available become obvious.

While tolerances in other regulators such as my aforementioned patented device are very critical and even a few thousandths of an inch variation can cause such devices to be rejected because they will not operate properly, in the present invention the tolerances are large and the reject rate in manufacture will be extremely low because of the wide latitude allowed in dimensions of critical areas.

Another important aspect which has been touched upon is that since the diaphragm used in the present invention is not put under tension during assembly it can merely be dropped into place in contrast to many existing arrangements where prestressing is required. As a consequence, the present invention lends itself better to automated assembly with reduced labor requirements and less concern for whether the diaphragm will "set" over a period of its shelf life.

I will be noted from FIG. 1 that regulator 24 is inserted into line 12 at some point below drip chamber 20.

If desired, the present invention can be incorporated into a drip chamber by modifying the latter to receive it with resulting savings in the cost of production.

Figure 9:
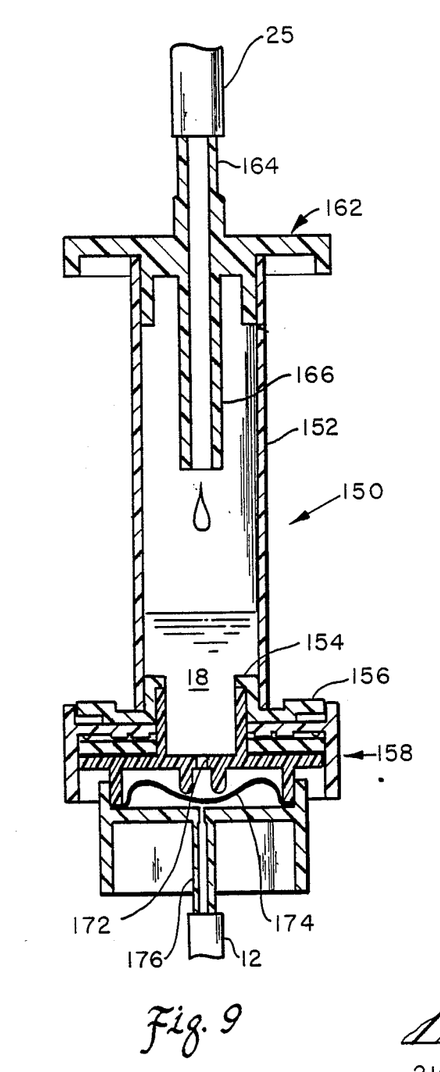
FIG. 9 is an elevation view in section of another embodiment of this invention wherein the regulator is incorporated into a drip chamber.

Such an embodiment is shown in FIG. 9 in which drip chamber regulator 150 connects tube 25 from the reservoir (not shown) to tube 12 leading to the hypodermic needle (not shown).

Regulator 150 consists of a cylindrical housing 152 open at both ends. Its lower end fits over rim 154 of annular stationary member 156 of regulator 158 which is identical to regulator 24 of FIGS. 1—8 except that inlet tube 42 is removed.

The upper end of housing 152 is fitted with a transition member 162 having an inlet tube 164 to engage tube 25 and a drip tube 166 which extends into housing 152. Transition member 162 is shaped in any convenient fashion to obtain a sturdy structure. A reservoir of the parenteral liquid 18 is formed within housing 152 above regulator 158 as illustrated for entry into the latter through inlet orifice 172 filling the chamber above diaphragm 174. Outlet tube 176 of regulator 158 delivers liquid 18 to tube 12.

In this embodiment just described it is seen that drip chamber 150 merely has to be connected between tube 12 and a reservoir to be used and functions in the same manner as regulator 24 described in connection with FIGS. 1-8.

The cost of manufacturing regulator 150 is significantly less than the use of a separate drip chamber and regulator as shown in FIG. 1 and in addition simplifies the procedures to be followed by the nurse, technician, or other health care worker.

The principles of the present invention may also be incorporated into an inline device made up of only three parts. This embodiment is illustrated in FIGS. 10—16.

Figure 10:
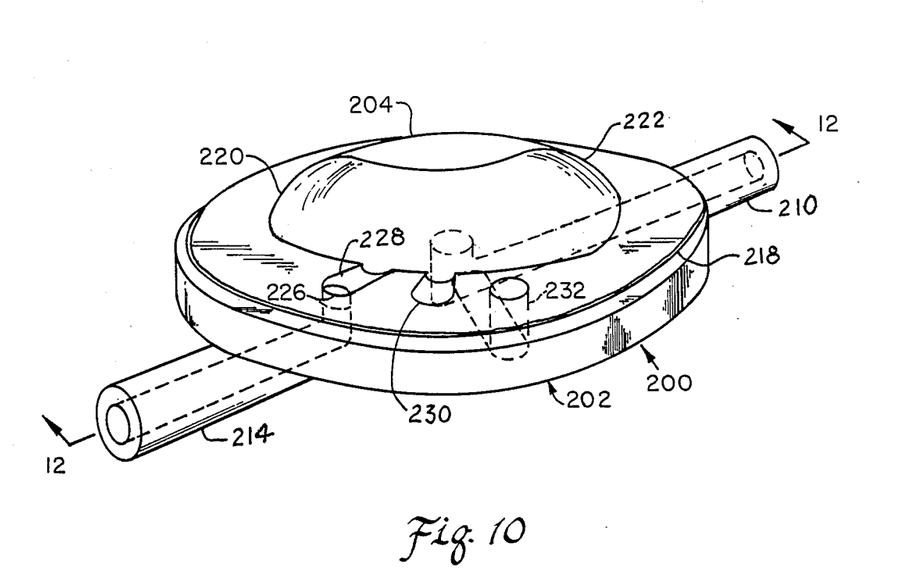
FIG. 10 is an isometric view of another embodiment with the upper housing removed.

Regulator 200 consists of a lower or inlet/outlet housing 202, a diaphragm and metering gasket 204, and an upper or metering disc and inlet chamber housing 206.

Lower housing 202 consists of a circular disc 208 with an outlet tube 210 extending from outlet orifice 212 centrally located in disc 208. Inlet tube 214 leads to an orifice 216 along the periphery of disc 208 for a purpose to be described below.

Diaphragm 204 consists of a circular flange 218 along the outer edge of a membrane 220 which consists of an arcuate torus 222 whose outer surface extends upwardly surrounding a bulbous section 224 whose lower or outer surface extends downwardly toward orifice 212.

Figure 11:
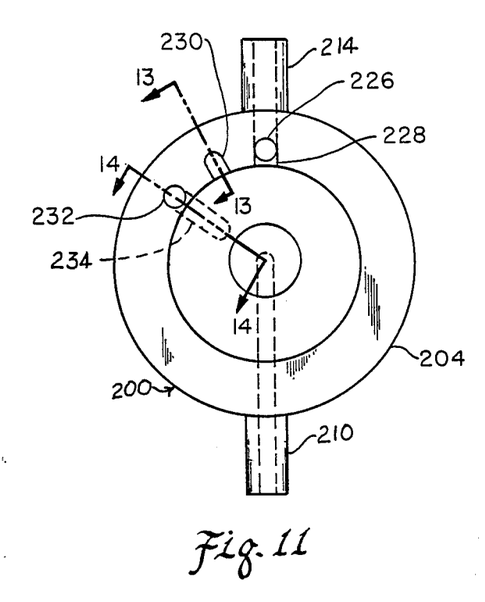
FIG. 11 is a plan view of the unit of FIG. 10.
Figure 13:
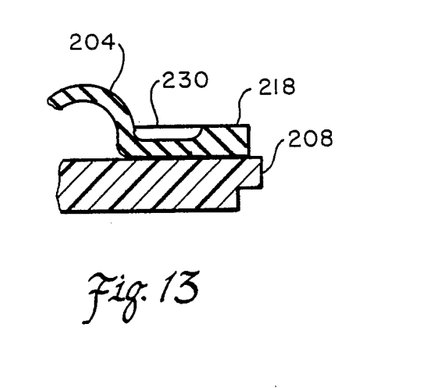
FIG. 13 is a section view taken along 13—13 of FIG. 11.
Figure 14:
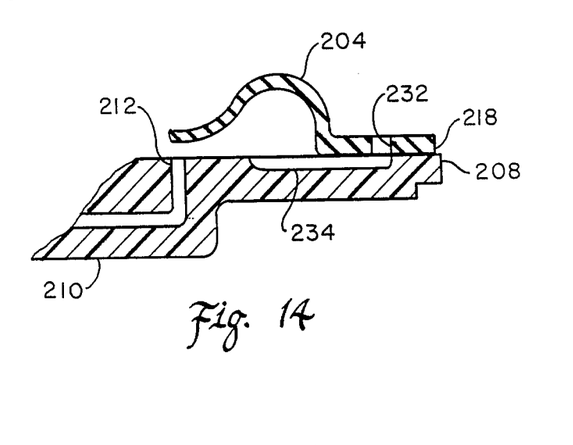
FIG. 14 is a section view taken along 14—14 of FIG. 11.
Figure 15:
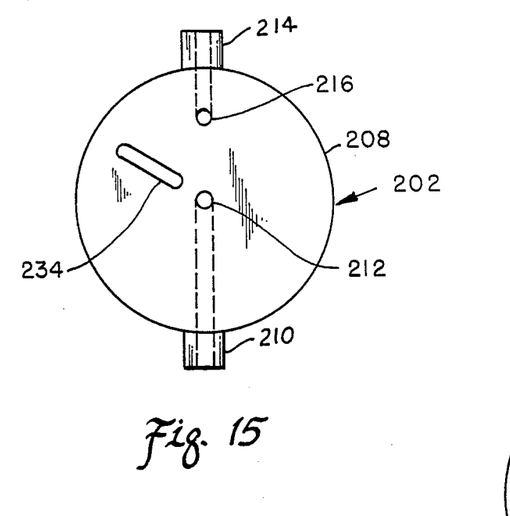
FIG. 15 is a plan view of the lower housing in the unit of FIG. 10.

It will be noted that flange 218 has an opening 226 aligned with orifice 216 communicating with inlet pipe 214. The top surface of flange 218 has a radially extending groove 228 communicating with opening 226 for a purpose to be described below. As seen in FIGS. 10, 11 and 13 diaphragm 204 is provided with a second radially extending groove 230 along the upper surface of flange 218 angularly offset or displaced from groove 228. In addition, diaphragm 204 is provided with a second opening 232 further angularly offset or displaced from groove 228 and from groove 230 as seen in FIG. 11. Opening 232 communicates under flange 218 with a radially extending groove 234 in the upper surface of disc 208 as seen in FIGS. 14 and 15. Communication between the various openings and grooves just described is provided by upper housing 206 which will now be described.

Figure 12:
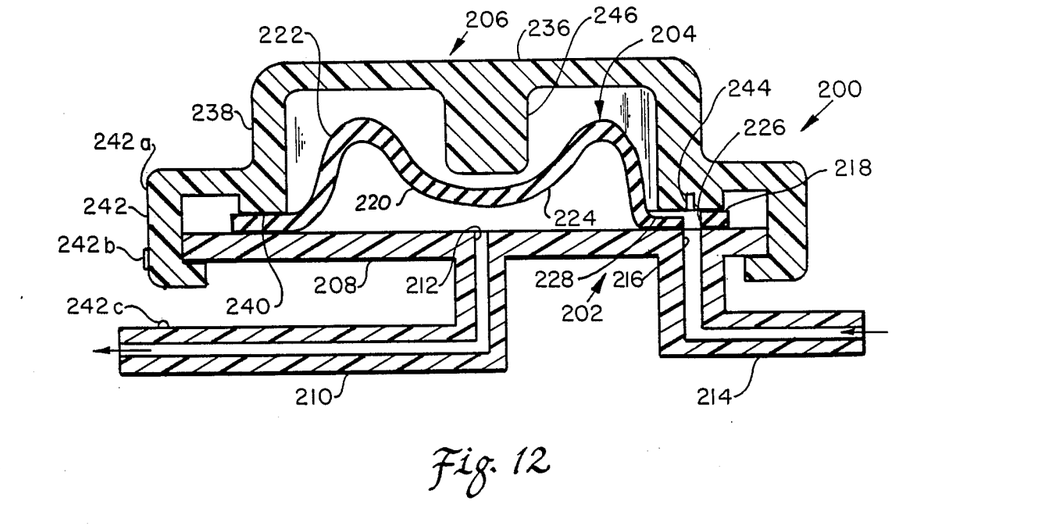
FIG. 12 is a section view along 12—12 of FIG. 10 with the upper housing present.

Upper housing 206 is circular with a top surface 236 and an annular downwardly extending wall 238 the bottom surface 240 of which clamps flange 218 to disc 208. Extending from side wall 238 is an annular U-shaped rim 242 to grasp the underside of disc 208 thereby to hold the assembly in place. This would be a snug fit and could be accomplished by making the parts so that they could be snapped together in a manner which is quite well known in the art. Lower and upper housings 202 and 206, respectively, may be made of suitable plastic capable of being snapped together, while diaphragm 204 would be made of rubber or similar flexible material for reasons which will become obvious.

Figure 16:
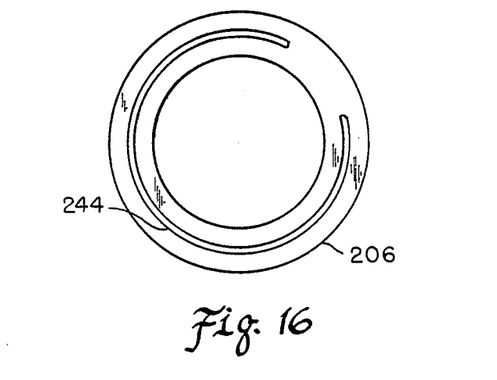
FIG. 16 is a view looking up at a portion of the upper housing of the unit in FIG. 12.

Bottom surface 240 of side wall 238 of upper housing 206 is provided with an annular, tapered metering groove 244 shown particularly in FIG. 16. Groove 244 is of varying depth as is groove 102 shown in FIGS. 6, 6a, and 6b in connection with the embodiment of this invention shown in FIGS. 1-8.

The purpose of metering groove 244 is to provide communication between opening or passageway 226 and groove 228, groove 230, and opening or passageway 232, although only communication between groove 230 and opening 232 is required for metering. Grooves 228 and 230 insure that liquid fills the space between housings 202 and 206 above membrane 220, herein referred to as the inlet chamber. Metering groove 244 transfers liquid to opening or passageway 232 down into groove 234 in disc 208 and into the space below membrane 220, herein referred to as the outlet chamber, as best illustrated in FIG. 14.

By rotating upper housing 206 manually, a rate of flow through regulator 200 can be established due to the fact the effective opening through metering groove 244 between groove 230 and passageway 232 is changed as the result of the variable depth of groove 244 in bottom surface 240 of side wall 238 in upper housing 206.

The outer surface 242a of U-shaped arm 242 may be provided with indicia 242b read in connection with an indicator mark 242c located on outlet tube 210 for calibration of regulator 200. If desired, any other means of providing such calibration may be employed.

The interior of upper housing 206 may be provided with an extension 246 to act as an anti-bolus device in the same manner as described for boss 48 described in connection with the embodiment of FIGS. 1—8.

The advantages of the embodiment shown in FIGS. 10—16 are that it is extremely economical to manufacture inasmuch as it consists of only three parts and assembly can be accomplished by merely snapping them together. At the same time it can be preset or calibrated at the factory for rate of flow, the diaphragm is unstressed during its shelf life so that no change in flow characteristic of the unit will occur, and is easy to use by the technician who sets up the I.V.

While only certain preferred embodiments of this invention have been described it is understood that many variations of this invention are possible without departing from the principles of this invention as defined in the claims which follow.

What is claimed is:

1. Apparatus for the I.V. administration of a parenteral liquid to a patient comprising:
   a. outlet means including an outlet orifice for discharging said parenteral liquid for application to said patient;
   b. inlet means for receiving said parenteral liquid;
   c. diaphragm means having a flange mounted between said inlet and outlet means and membrane means enclosed by said flange separating incoming parenteral liquid from outgoing parenteral liquid for maintaining the rate of discharge of said parenteral liquid through said outlet orifice;
   d. means for bypassing flow of said parenteral liquid from said inlet means to said outlet means around said membrane means;
   e. selecting means entirely contained within said apparatus for selecting the rate of flow of said liquid through said apparatus independent of the pressure of parenteral liquid at either the inlet or outlet side of said apparatus; and
   f. said membrane means in the absence of liquid flow being shaped in the form of an annular arcuate torus the outer surface of which faces said inlet means, the portion of said membrane means surrounded by said torus forming a bulbous section which is curved outwardly in its resting state in the direction of and controls flow through said outlet orifice, said membrane means in the absence of any liquid in its resting state being unstressed and making no contact with any part of said apparatus thereby remaining unstressed during shipping and storage prior to use and permitting rolling of said torus during flow of liquid through said apparatus as a result of pressure differential across said membrane means so that said bulbous section moves toward and away from said outlet orifice in response to pressure differential across said membrane means.

2. The apparatus of claim 1 having means between said inlet means and said diaphragm means to prevent reversal of flow through said apparatus and delivery of a bolus of said parenteral liquid through said outlet means.

3. The apparatus of claim 2 in which said inlet means has an inlet orifice and said means to prevent delivery of a bolus comprises annular boss means surrounding said inlet orifice extending toward but not contacting said membrane means during normal operation of said apparatus.

4. Apparatus for establishing and maintaining constant the flow rate of liquid passing therethrough comprising:
 a. inlet and outlet means for receiving and discharging said liquid, respectively;
 b. diaphragm means of flexible material mounted between and separating said inlet means from said outlet means including means to permit flow of liquid therethrough;
 c. said diaphragm means comprising a membrane unstressed in the absence of liquid surrounded by a flange clamped between said inlet and outlet means, said membrane shaped in the form of an arcuate torus in the unstressed condition the outer surface of which faces said inlet means, the portion of said membrane surrounded by said torus forming a bulbous section the outer surface of which faces said outlet means, said torus and bulbous section being free of contact with any part of said apparatus to permit rolling of said torus;
 d. said inlet means having inlet orifice means for discharging said liquid into the region above said diaphragm means;
 e. said outlet means having an outlet orifice opposite said bulbous section, said bulbous section regulating the rate of flow through said outlet orifice by moving as a result of rolling of said torus in response to differential liquid pressure across said membrane to maintain constant the flow rate; and
 f. means included in said apparatus for selecting the rate of flow of said liquid to be maintained through said apparatus.

5. The apparatus of claim 4 having means to prevent flow reversal therethrough.

6. The apparatus of claim 4 having anti-bolus means to prevent the delivery of a surge of liquid through said outlet means.

7. The apparatus of claim 6 in which said anti-bolus means comprises annular boss means surrounding said inlet orifice means extending toward but not contacting said membrane.

8. The apparatus of claim 7 in which said membrane in the absence of liquid in its resting condition makes no contact with any other part of said apparatus other than said flange being clamped thereby remaining unstressed during shipment and storage.

9. The apparatus of claim 4 in which said flow selecting means adjusts flow of liquid through said diaphragm means.

10. The apparatus of claim 9 in which said flange of said diaphragm means includes a passageway for the flow of said liquid therethrough, means in said outlet means for providing communication between said passageway and the region on the outlet side of said membrane for flow of liquid out through said outlet orifice, and said selecting means including a rotatable means for changing the effective size opening between said passageway and the region on the inlet side of said membrane.

11. The apparatus of claim 10 in which said inlet means and said rotatable means are provided with indicia positioned by rotation of said rotatable means to identify the flow rate to be selected.

12. The apparatus of claim 11 in which is mounted a stationary gasket between said inlet means and said rotatable means having a pair of passageways circumferentially displaced from each other, and said rotatable means is provided with a groove of varying cross section for providing communication between said pair of passageways, the rotation of said rotatable means effectively altering the rate of flow through said apparatus.

13. The apparatus of claim 12 having anti-bolus means to prevent delivery of a surge of liquid through said outlet means comprising annular boss means surrounding said inlet orifice means extending toward but not contacting said membrane.

14. The apparatus of claim 4 in which said membrane in the absence of liquid in its resting condition makes no contact with any other part of said apparatus other than said flange being clamped thereby remaining unstressed during shipment and storage.

15. The apparatus of claim 4 having a drip chamber mounted on said inlet means wherein a reservoir of said liquid is formed with and above said diaphragm.

16. A flow regulator for a liquid comprising:
 a. rotatable upper housing means containing means to establish a rate of flow through said regulator;
 b. stationary lower housing means containing flow inlet means, flow outlet means, and an outlet orifice through which said liquid passes into said flow outlet means; and
 c. stationary diaphragm means comprising a membrane surrounded by a flange clamped between said upper and lower housing means, so that both the flow inlet means and the flow outlet means are on the same side of said diaphragm, said membrane shaped in the form of a semi-circular arcuate torus in the unstressed condition the outer surface of which faces said upper housing means, the portion of said membrane surrounded by said torus forming a bulbous section the outer surface of which faces said outlet orifice forming an outlet chamber between said bulbous section and said outlet orifice, an inlet chamber being formed above said bulbous section, said arcuate torus and bulbous section being free of contact with any part of said housing means to permit rolling of said torus;
 d. flow means in said diaphragm means for transferring said liquid from said inlet means into said inlet and outlet chambers; and
 e. control means in said upper housing means for establishing said rate of flow by selecting the effective opening in said flow means for the transfer of said liquid, said effective opening being obtained by rotation of said upper housing means.

17. The regulator of claim 16 in which said upper housing means includes anti-bolus means to prevent surges of said liquid through said outlet orifice.

18. The regulator of claim 16 in which said flow means includes spaced passageway means in said flange, and said control means includes a tapered groove communicating with both said spaced passageway means, said upper housing being rotatable to adjust the effective opening of said tapered groove exposed to said passageway means.

* * * * *